United States Patent [19]
Gotoh

[11] Patent Number: 5,931,572
[45] Date of Patent: Aug. 3, 1999

[54] HEAD LAMP DEVICE FOR VEHICLE

[75] Inventor: Shinichiro Gotoh, Wako, Japan

[73] Assignee: Honda Giken Kogyo Kabushiki Kaisha, Tokyo, Japan

[21] Appl. No.: 08/858,361

[22] Filed: May 19, 1997

[30]  Foreign Application Priority Data

May 20, 1996 [JP] Japan ................................. 8-124186

[51] Int. Cl.$^6$ ................................................. B60Q 1/08
[52] U.S. Cl. ........................... 362/466; 362/272; 362/276
[58] Field of Search .................................. 340/466, 467,
340/575, 576; 362/37, 43, 464, 465, 466,
276, 802, 271, 272

[56]  References Cited

U.S. PATENT DOCUMENTS

| | | | |
|---|---|---|---|
| 4,604,611 | 8/1986 | Seko et al. | 340/576 |
| 4,858,080 | 8/1989 | Oikawa | 362/466 |
| 5,060,120 | 10/1991 | Kobayashi et al. | 362/465 |
| 5,138,540 | 8/1992 | Kobayashi et al. | 362/466 |
| 5,453,929 | 9/1995 | Stove | 340/575 |
| 5,499,168 | 3/1996 | Cochard et al. | 362/466 |
| 5,588,733 | 12/1996 | Gotou | 362/37 |
| 5,660,454 | 8/1997 | Mori et al. | 362/466 |

FOREIGN PATENT DOCUMENTS

| | | |
|---|---|---|
| 62-77249 | 4/1987 | Japan . |
| 314742 | 1/1991 | Japan . |

*Primary Examiner*—Alan Cariaso
*Attorney, Agent, or Firm*—Carrier, Blackman & Associates, P.C.; Joseph P. Carrier; William D. Blackman

[57]  ABSTRACT

A head lamp device for a vehicle capable of changing a lighting region in front of the vehicle in rightward and leftward directions is provided. The device comprises a head lamp, lighting region changing means for changing the lighting region of the head lamp, strain degree detecting means for detecting degree of strain of the driver, and control means for controlling the lighting region changing means on the basis of information detected by the strain degree detecting means. The control means adjusts the amount and/or the speed of change of the lighting region in accordance with degree of strain of the driver. The change of the lighting region can be carried out naturally without sense of incongruity in view of degree of strain of the driver.

15 Claims, 6 Drawing Sheets

HEAD LAMP DEVICE FOR VEHICLE

BACKGROUND OF THE INVENTION

The present invention relates to light distribution control of a head lamp of a vehicle for changing a lighting region produced by the head lamp toward right and left direction.

DESCRIPTION OF RELEVANT ART

Hitherto, various devices for changing a lighting region of a vehicles head lamp right and left have been proposed. Almost all of the devices change the lighting region in accordance with a steering angle of a steering wheel (Japanese laid-open patent publications No. Sho 62-77249, No. Hei 3-14742 etc.). According to the devices, the lighting region of the head lamp is changed toward a direction of steering to increase lighting of the direction in which a vehicle is just going to advance.

In the Japanese laid-open patent publication No. Hei 3-14742, pertinent lighting angles corresponding to steering angles are determined beforehand and stored as a map, and controls for changing the lighting region are carried out on the basis of the map.

However, in the above-mentioned prior arts, no condition of the driver himself is taken into consideration. Therefore, when the driver is strained because of the state of a road in front or the state of operation of the vehicle, he may feel sometimes that a change of the lighting region occurs too slowly, or when a degree of the strain is low conversely, he may feel sometimes that a change of the lighting region is fast and troublesome.

Namely, when the driver is strained, a moving speed of his eye is fast, so that even if a change of the lighting region is carried out large and fast correspondingly, there is no sense of incongruity or rather it desirably meets the driver's sense and intention. On the other hand, when the degree of the drivers strain is low, movement of his eye are few and slow, so that even if a change of lighting region is slight, it can be perceived sensitively and, therefore, if the change of lighting region is large or fast, the driver has a sense of incongruity and feels troublesome.

SUMMARY OF THE INVENTION

The present invention has been accomplished in view of the foregoing and it is an object of the present invention to provide a head lamp device for a vehicle in which change of the lighting region can be carried out naturally without any sense of incongruity in view of a degree of strain of the driver.

In order to accomplish the aforesaid object, the present invention provides a head lamp device for a vehicle capable of changing a lighting region in front of the vehicle in rightward and leftward directions. The device comprises a head lamp lighting region changing means for changing the lighting region of the head lamp; strain degree detecting means for detecting a degree of strain of a driver; and control means for controlling the lighting region changing means base on information detected by the strain degree detecting means, and the control means adjusts at least one of amount of change and speed of change of the lighting region in accordance with the detected degree of strain of the driver.

Since at least one of amount of change and speed of change of the lighting region is adjusted in accordance with the degree of strain of the driver, a pertinent change of the lighting region which does not give the driver a sense of incongruity and meets the driver's sense and intention is possible.

The strain degree detecting means may detect degree of strain of the driver by analyzing movement of the eye(s) of the driver. Namely, when the eye of the driver moves violently or rapidly it is judged that the degree of strain is high and when the eye moves slowly, it is judged that the degree of strain is low.

The strain degree detecting means may also detect degree of strain of the driver by analyzing the heart rate or skin electric potential of the driver. Generally, when the heart rate is high or the skin electric potential is low, the degree of strain can be judged high, and when the heart rate is low or the skin electric potential is high, the degree of strain can be judged low.

The present invention provides also a head lamp device for a vehicle capable of changing a lighting region in front of the vehicle in rightward and leftward directions, comprising lighting region changing means for changing the lighting region of the head lamp; operation state detecting means for detecting an operation state of the vehicle; strain degree judging means for judging a degree of strain of the driven by analyzing information detected by the operation state detecting means; and control means for controlling the lighting region changing means base on of information judged by the strain degree judging means and adjusting at least one of amount of change and speed of change of the lighting region in accordance with the judged degree of strain of the driver.

Since the strain degree judging means judges the degree of strain of the driver by analyzing information detected by the operation state detecting means and the control means changes the lighting region on the basis of the degree of strain, the lighting region can be changed in accordance with the degree of strain of the driver.

The operation state detecting means may be a vehicle speed sensor for detecting vehicle speed and the strain degree judging means may judge the degree of strain of the driver by analyzing the vehicle speed detected by the vehicle speed sensor. When speed or acceleration of the vehicle is high or low, the degree of strain can be judged respectively high or low. Thus a change of the lighting region in accordance with the degree of strain is possible.

The operation state detecting means may also be a steering angle sensor for detecting a steering angle and/or steering speed of the vehicle and the strain degree judging means may judge the degree of strain of the driver by analyzing the steering angle and/or steering speed detected by the steering angle sensor. When the steering angle speed is high or low, the degree of strain can be judged respectively high or low. Thus a change of the lighting region in accordance with the degree of strain of the driver is possible.

The operation state detecting means may also be a turning movement sensor for detecting turning movement of the vehicle body, and the strain degree judging means may judge the degree of strain of the driver by analyzing the turning movement detected by the turning movement sensor. When lateral acceleration or yaw rate of the vehicle body is large, the degree of strain can be judged to be high, and when the lateral acceleration or yaw rate is small, the degree of strain can be judged to be low. Thus a change of the lighting region in accordance with degree of strain is possible.

The present invention provides further a head lamp device for a vehicle capable of changing a lighting region in front of the vehicle in rightward and leftward directions, comprising lighting region changing means for changing the lighting region of the head lamp; map information outputting means for outputting map information representing a map; present position detecting means for detecting a present position of a proper vehicle on the map; strain degree judging means for judging a degree of strain of the driver base on the map information outputted by the map information outputting means and the present position of the proper vehicle detected by the present position detecting means; and control means for controlling the lighting region changing means base on information on the degree of driver strain judged by the strain degree judging means and adjusting at least one of amount of change and speed of change of the lighting region in accordance with the degree of strain of the driver judged from a state of road in front of the proper vehicle.

From a state of the road on which the proper vehicle is running, the degree of strain of the driver who is watching the state can be judged. Thus a change of the lighting region in accordance with the degree of strain is possible.

DETAILED DESCRIPTION OF THE PREFERRED EMBODIMENT

Hereinafter, a preferred embodiment of the present invention will be described with reference to FIGS. 1 to 8.

Figure 1:
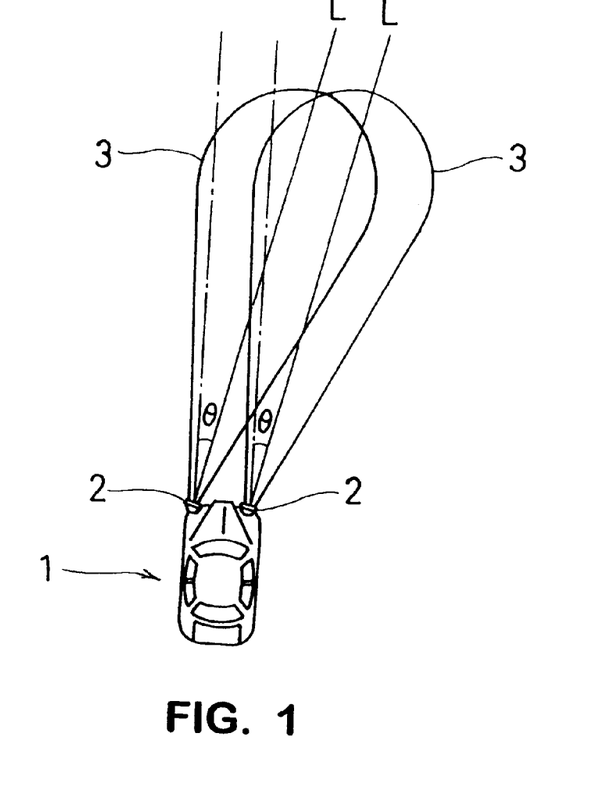
FIG. 1 is a view showing a vehicle having a head lamp device of one preferred embodiment of the present invention as viewed from above.

A vehicle 1 of the preferred embodiment has head lights 2 for lighting the space in front of the vehicle installed such that they are swingable in a rightward and leftward horizontal direction. FIG. 1 is a view for showing the vehicle 1 from above and in this figure, the right and left head lights 2, 2 are swung rightward so as to cause the right forward regions to become lighting regions 3, 3.

The right and left head lights 2, 2 are swung together in the same direction by the same angle and as shown in FIG. 1, angles of their optical axes L, L with respect to an advancing direction of the vehicle, i.e. lighting angle, are both set to be $\theta$. Regarding the angle $\theta$, that on the right side with respect to the advancing direction is given plus sign and that on the left side is given minus sign.

Alternatively, only a head light on the turning side may be swung or the right and left head lights may be swung by respective angles different from each other.

Figure 2:
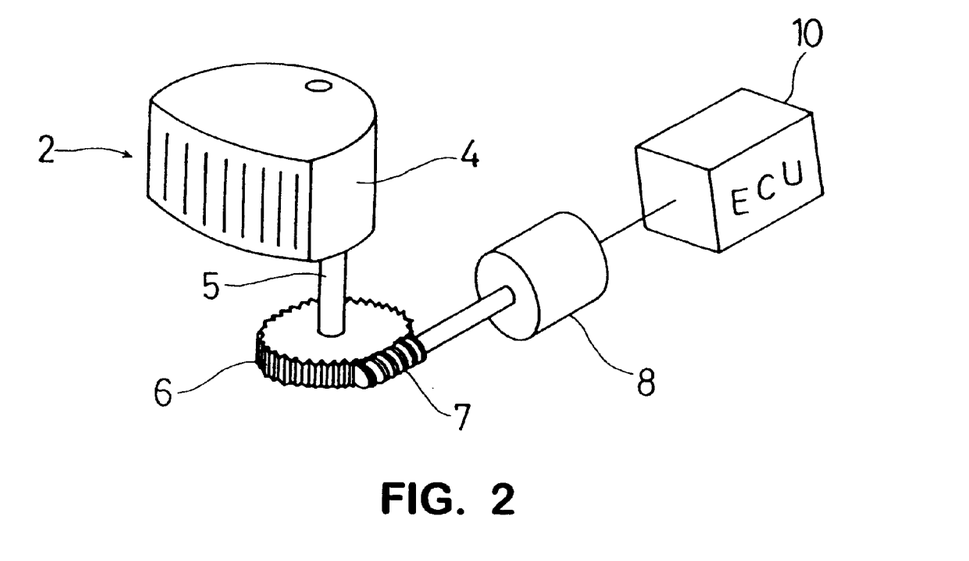
FIG. 2 is a schematic perspective view showing a swinging mechanism for a head lamp of the preferred embodiment of FIG. 1.

A swinging mechanism for swinging the head light 2 in the preferred embodiment is schematically shown in FIG. 2, wherein a lamp unit 4 of the head light 2 is fixed to a rotary shaft 5, and a worm gear 7 formed at the end of a driving shaft of a motor 8 is engaged with a worm wheel 6 fitted to the rotary shaft 5.

Accordingly, the lamp 4 is swung together with the rotary shaft 5 through an engagement between the worm gear 7 and the worm wheel 6 under a driving force of the motor 8. The motor 8 is controlled for its driving action by a light distributing control ECU 10.

The vehicle 1 has a CCD camera 11 (FIG. 4) arranged in the vicinity of an upper end or lower end of a front window in front of a driver's seat (for example on an instrument panel) to take a picture of driver's face, particularly his eye.

Figure 3:
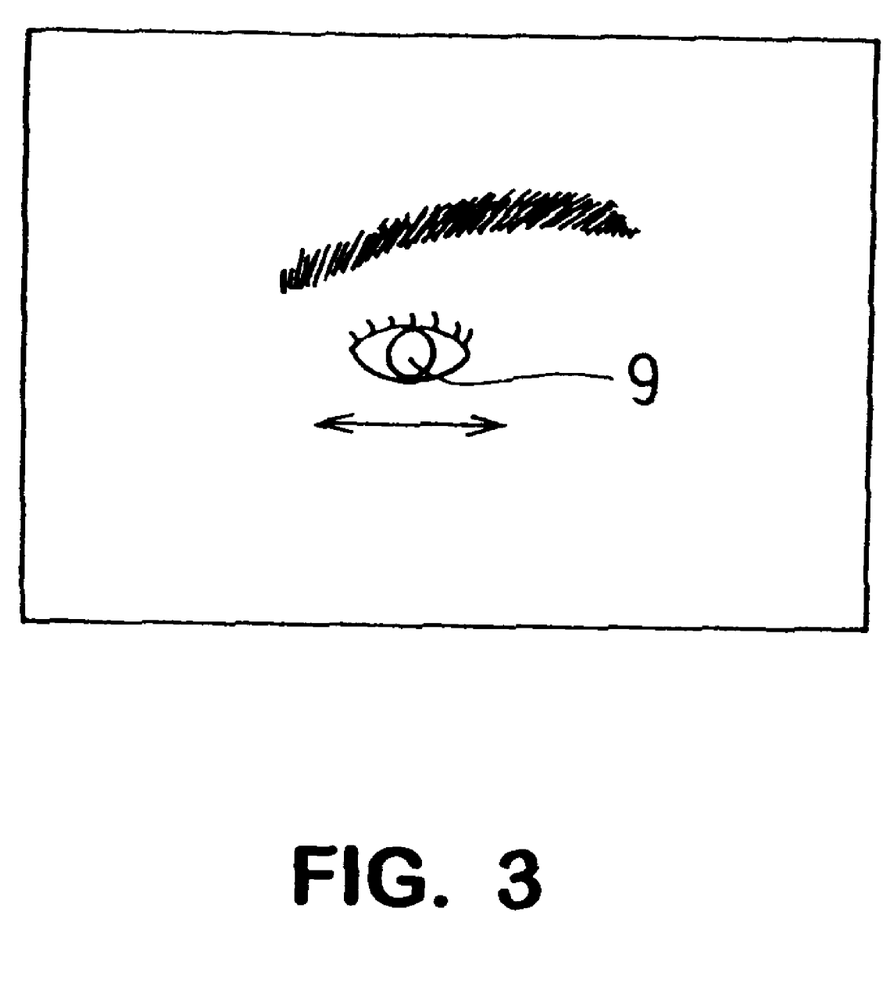
FIG. 3 is a view showing a picture taken by a CCD camera.

FIG. 3 shows a picture taken by the CCD camera 11. This picture information is inputted into a picture processing apparatus 12 which processes the picture, analyzes movement of the driver's eye, particularly the eyeball thereof, to calculate a moving speed of the eye and outputs a result of the calculation to the light distribution control ECU 10. The eye moving speed Ve is used as a measure of degree of strain of the driver and if the eye moving speed is faster, the degree of strain of the driver is judged higher correspondingly.

Figure 4:
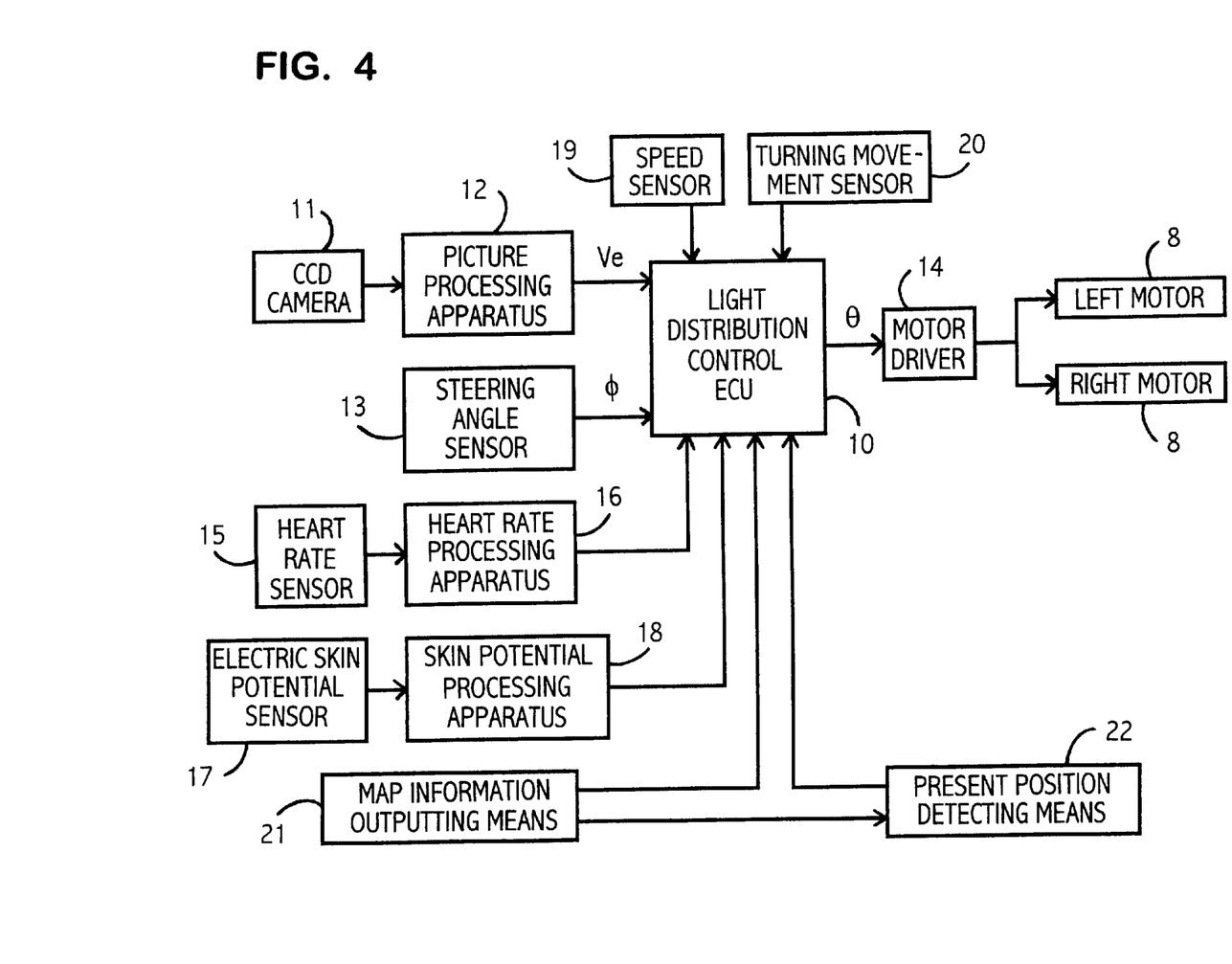
FIG. 4 is a rough block diagram of a control system.

FIG. 4 is a rough block diagram of a control system according to the present embodiment controlled by the light distribution control ECU 10. Into the light distribution control ECU 10 is inputted a detected steering angle $\phi$ from a steering angle sensor 13 for detecting a steering angle of a steering wheel, as well as the eye moving speed Ve from the picture processing apparatus 12.

The light distribution control ECU 10 finally decides a required amount of change of the lighting region, that is a lighting angle $\theta$, on the basis of the eye moving speed Ve and the steering angle $\phi$, and outputs a control signal to the motor driver 14 for realizing the lighting angle $\theta$. The motor driver 14 drives and controls the right and left motors 8, 8.

A procedure of lighting region control according to the above-mentioned control system will be described with reference to a flow chart of FIG. 5.

At first, a target control angle $\theta_1$ is decided from a steering angle $\phi$ based on a $\phi$-$\theta_1$ map as indicated in step 1.

Figure 6:
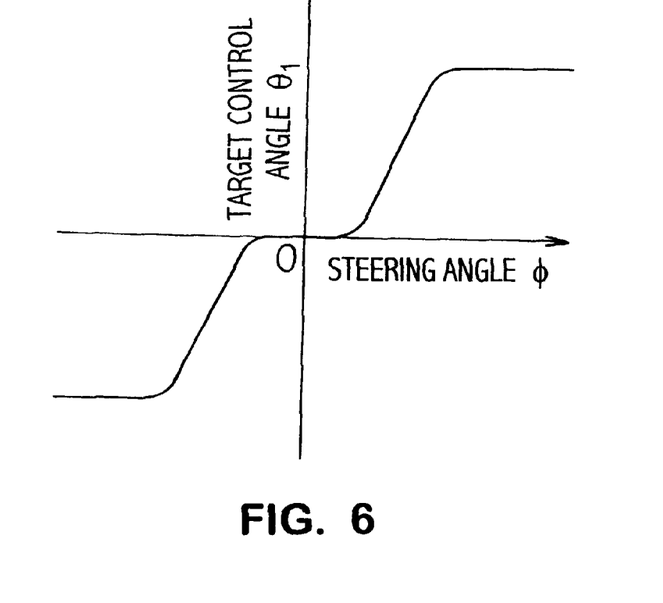
FIG. 6 is a coordinate expression of a $\phi$-$\theta_1$ map for showing correspondence between a steering angle $\phi$ and a target control angle $\theta_1$.

In the $\phi$-$\theta_1$ map, a target control angle $\theta_1$ which is a lighting angle to be aimed is set in regard to a steering angle $\phi$ beforehand, and FIG. 6 is a coordinate expression thereof. A non-responsive zone in which the target control angle $\theta_1$ is not changed is provided at a range where the steering angle $\phi$ is small. Except for the non-responsive zone, the target control angle $\theta_1$ increases or decreases in proportion to the steering angle $\phi$, generally, but is kept constant if the steering angle $\phi$ rises above a limit in either direction.

Figure 7:
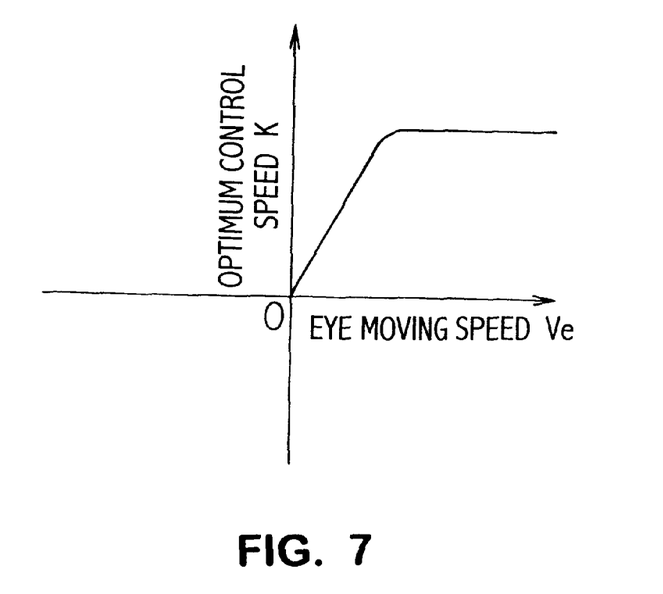
FIG. 7 is a coordinate expression of a Ve-K map for showing correspondence between an eye movement speed Ve and a optimum control speed K.

After the target control angle $\theta_1$ is decided from the steering angle $\phi$ based on the $\phi$-$\theta_1$ map, the flow advances to Step 2 for deciding an optimum control speed K from the eye moving speed Ve based on a Ve-K map. In the Ve-K map, an optimum control speed K of the lighting angle is set in regard to an eye moving speed Ve, and FIG. 7 is a coordinate expression thereof.

The optimum control speed K is proportional to the eye moving speed Ve and as the eye moving speed Ve increases, the optimum control speed K also increases. However, if the eye moving speed Ve rises above a limit, the optimum speed K is kept constant After the target control angle $\theta_1$ and the optimum control speed K are decided, the flow advances to Step 3 for comparing a target control speed $|\theta_1-\theta_0|/d$ with the optimum control speed K. $\theta_0$ is the lighting angle at present and d is a processing time for 1 cycle of this control routine.

Therefore, the target control speed $|\theta_1-\theta_0|/d$ means a rate of change of the lighting angle required for changing the lighting angle from the present lighting angle $\theta_0$ to the target control angle $\theta_1$ during 1 cycle. When the target control speed $|\theta_1-\theta_0|/d$ is larger than the optimum control speed K, the flow advances to Step 4 where the target control speed $\theta_1$ and the present lighting angle $\theta_0$ are compared to discriminate whether the light axis is to be changed rightward or leftward. If rightward, the flow advances to Step 5 and a final control angle $\theta$ for 1 cycle is set at $\theta_0+K\times d$. If leftward, the flow advances to Step 6 and the final control angle $\theta$ for 1 cycle is set at $\theta_0-K\times d$.

Namely, when the target control speed $|\theta_1-\theta_0|/d$ exceeds the optimum control speed K, the final control angle $\theta$ is decided so as to restrain changing speed of the lighting angle to the optimum control speed K for avoiding the situation that the changing speed of the lighting angle becomes extremely large and gives the driver a sense of incongruity. Since the optimum control speed K is proportional to the eye moving speed Ve, when the eye moving speed Ve is fast and degree of strain of the driver is supposed to be high, the changing speed of the lighting angle is also made fast to meet the driver's sense and intention.

On the other hand, when the target control speed $|\theta_1-\theta_0|/d$ does not reach the optimum control speed K at Step 3, the flow jumps to Step 7 where the final control angle $\theta$ is set at the target control angle $\theta_1$. That is, changing of the lighting region is carried out at the target control speed $|\theta_1-\theta_0|/d$.

Figure 8:
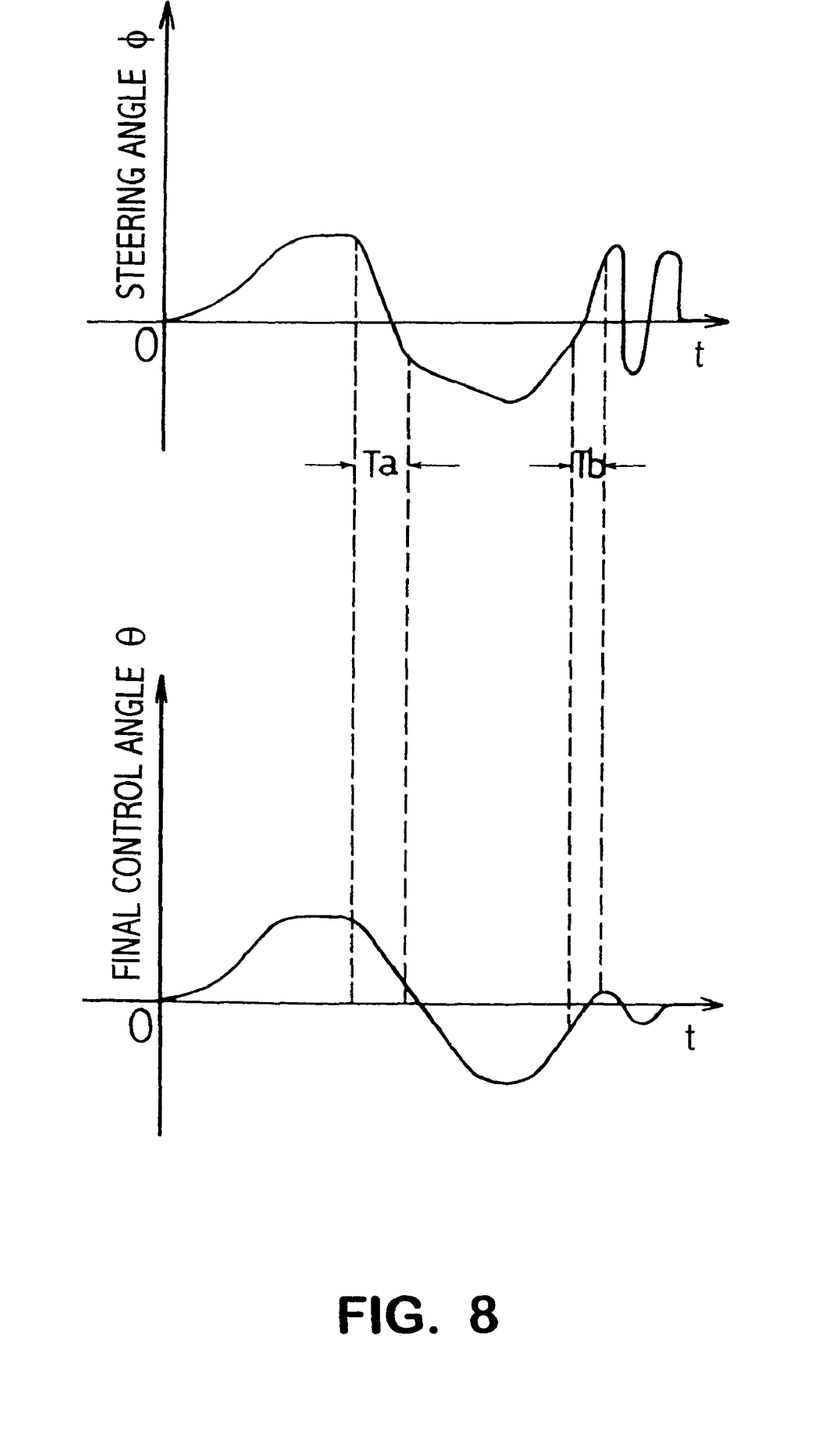
FIG. 8 is a view showing change of the steering angle $\phi$ and change of the target control angle $\theta$ in comparison.

A control signal based on the final control angle $\theta$ decided in the manner as described above is outputted to the motor driver 14 for driving and controlling the motor 8. FIG. 8 shows an example of change of the final control angle $\theta$. The upper portion of FIG. 8 shows change of the steering angle $\phi$ and the lower portion shows change of the final control angle $\theta$. The both have a common horizontal time axis.

The target control angle $\theta_1$ also changes in a similar manner as the steering angle $\phi$ since the target control angle $\theta_1$ is proportional to the steering angle $\phi$ except in the nonresponsive zone. When the steering angle $\phi$ changes gently, the final control angle $\theta$ coincides with the target control angle $\theta_1$ (Step 7 in FIG. 5), therefore the final control angle $\theta$ changes in a similar manner as the steering angle $\phi$.

Figure 5:
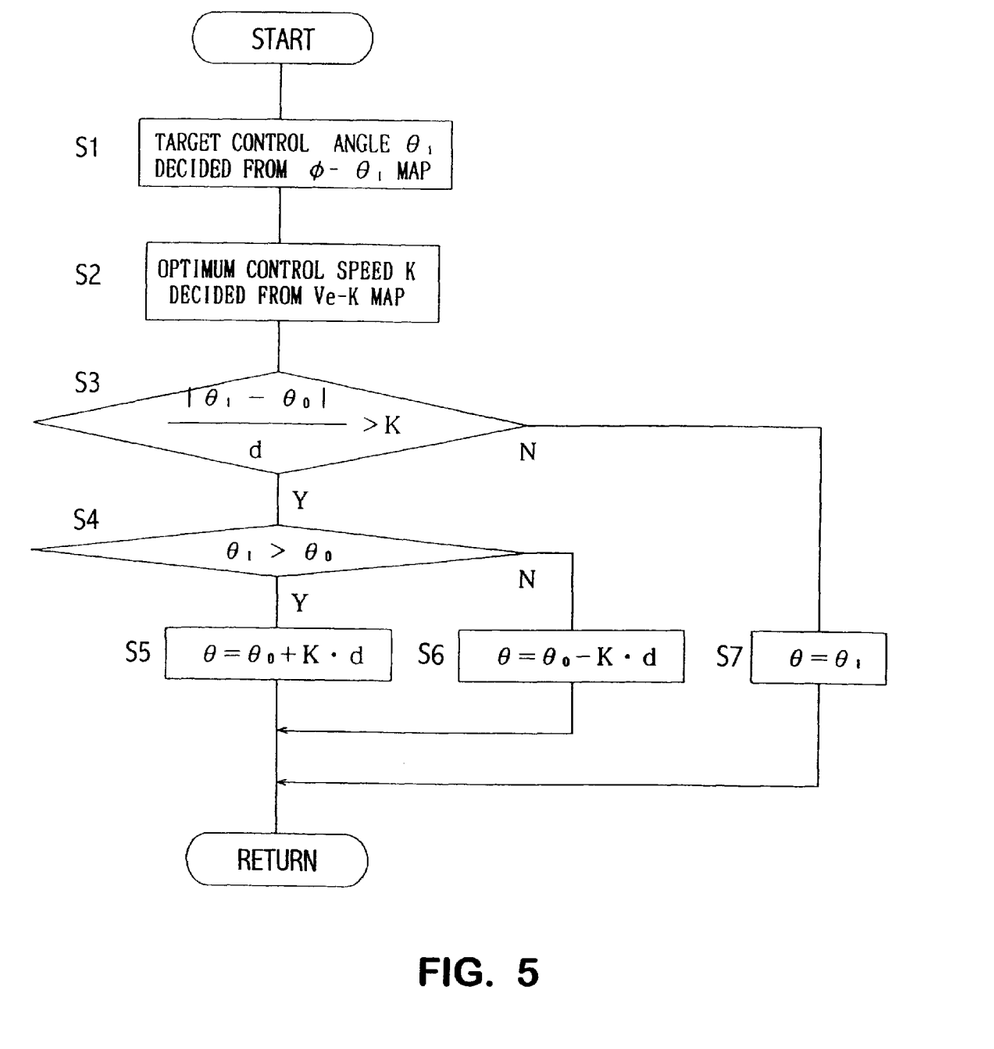
FIG. 5 is a flow chart showing a procedure for changing the light region.

However, when the steering angle $\phi$ changes rapidly (Ta and Tb sections in FIG. 8), the final control angle changes gently being restrained to the optimum control speed K (Step 5 or 6 in FIG. 5).

In case that the steering handle is returned rapidly as in the Ta and Tb sections in FIG. 8, according to a conventional technique the lighting region is also changed rapidly to give the driver a sense of incongruity. According to the present embodiment, however, the lighting region is changed at a smoothed speed not giving the driver the sense of incongruity because the change of the final control angle is restrained to the optimum control speed K.

In addition, since the optimum control speed K is proportional to the eye moving speed Ve, the lighting region is changed at a speed suitable for the degree of strain of the driver to meet the driver's sense and intention.

Though degree of strain of the driver is judged from the eye moving speed Ve in the above embodiment, heart rate of the driver may be measured by sensor 15 in place of the eye moving speed Ve. In this case, it is necessary to attach a heart rate sensor to the driver's arm for example.

The degree of strain is judged from fluctuation of intervals of heartbeats or the like by analyzing the heart rate using apparatus 16, and a map of the optimum control speed K corresponding to the degree of strain based on the driver's heart rate is prepared beforehand similarly to the case of the eye moving speed Ve. This optimum control speed is used for controlling change of the lighting region in such manner that when the degree of strain is high the lighting region is changed fast and when the degree of strain is low the lighting region is changed slowly.

Skin electric potential of the driver also shows the degree of strain as measured by sensor 17. When the degree of strain is high, the driver's hand or the like is sweaty, which lowers the skin electric potential. Therefore, if the skin electric potential of the driver is measured, the result can be applied using apparatus 18 in the same way as the abovementioned eye moving speed Ve and heart rate.

Further, a brain wave or the like is also applicable.

In the foregoing, degree of strain of the driver is judged directly from a change of his own body, however it is also possible to judge the degree of strain from an operation state of the vehicle indirectly. For example, when the vehicle speed is high, the degree of strain can be judged high because the driver is required to perform more careful operation as the vehicle speed increases. Or the degree of strain can be judged by analyzing change of the vehicle speed too, to some extent.

Similarly, the degree of strain can be judged by analyzing movement of the steering wheel, that is, change of the steering angle $\phi$ too. When the steering angle $\phi$ changes frequently, degree of strain can be supposed high, generally. Further, degree of strain of the driver can be judged by analyzing turning movement of the vehicle body such as yaw rate or lateral acceleration G.

Preferably, a map of the optimum control speed K corresponding to the degree of strain of the driver analyzed from the operation state of the vehicle is prepared beforehand to be applied for controlling change of the lighting region in the same manner as the foregoing.

In a vehicle having a navigation system mounted therein, map information is stored and then output using means 21 and a present position of the proper vehicle on the map can be detected by means 22 and, therefore, a computer can recognize a state in front of the vehicle of a road on which the vehicle is now travelling. From the state of the road in front of the vehicle such as a curve, a straight course or a crossing, the degree of strain of the driver can be judged to some extent.

In case of curves continuing or at a crossing, it may be judged that degree of strain of the driver increases and in case of straight courses continuing, may be judged that the degree of strain is low. Therefore, a pertinent light distribution control giving no sense of incongruity to the driver can be carried out by inputting information of the state of the road in front of the vehicle from the navigation system, analyzing the information to judge the degree of strain of the driver and applying the result to control of change of the lighting region in the same manner as aforementioned control based on detected characteristics of the driver and the detected operation states of the vehicle. Although there has been described what is at present considered to be the preferred embodiment of the invention, it will be understood by those skilled in the art that variations and modifications may be made thereto without departing from the spirit or essence of the invention. The scope of the invention is, therefore, indicated by the appended claims, rather than the foregoing description of the presently preferred embodiment.

What is claimed is:

1. A head lamp device for a vehicle capable of changing a lighting region in front of the vehicle in rightward and leftward directions, said device comprises:

a head lamp;

lighting region changing means for changing a lighting region of the head lamp;

strain degree judging means for judging a degree of strain of a driver; and control means for controlling said lighting region changing means based on information judged by said strain degree judging means, and said control means adjusts at least one of amount of change and speed of change of the lighting region in accordance with the judged degree of strain of the driver.

2. A head lamp device for a vehicle as defined in claim 1, wherein said strain degree judging means comprises means for detecting the degree of strain of the driver by detecting and analyzing a characteristic of the driver.

3. A head lamp device for a vehicle as claimed in claim 2, wherein said strain degree detecting means detects the degree of strain of the driver by analyzing movement of an eye of the driver.

4. A head lamp device for a vehicle as claimed in claim 2, wherein said strain degree detecting means detects the degree of strain of the driver by analyzing at least one of heart rate and skin electric potential of the driver.

5. A head lamp device for a vehicle as claimed in claim 2, wherein said detecting means detects at least one of movement of an eye of the driver, heart rate of the driver and skin electric potential of the driver.

6. A head lamp device for a vehicle as claimed in claim 1, wherein said strain degree judging means comprises operation state detecting means for detecting an operation state of the vehicle, and said strain degree judging means judges the degree of driver strain by analyzing information detected by said operation state detecting means.

7. A head lamp device for a vehicle as claimed in claim 6, wherein said operation state detecting means detects at least one of vehicle speed, a steering angle of the vehicle, and turning movement of the vehicle.

8. A head lamp device for a vehicle as claimed in claim 1, wherein said strain degree judging means comprises map information outputting means for outputting map information representing a map and present position detecting means for detecting a present position of a proper vehicle on the map; said strain degree judging means determines a state of road in front of the proper vehicle based on the map information output by said map information outputting means and the detected proper position of the vehicle, and said strain degree judging means judges the degree of driver strain by analyzing the state of road in front of the proper vehicle.

9. A head lamp device for a vehicle as claimed in claim 1, wherein said control means determines at least one of a target amount of change and a target speed of change of the lighting region based on the judged degree of driver strain, and said control means adjusts said at least one of said amount of change and said speed of change of said lighting region based on a comparison of said at least one of said target amount of change and said target speed of change to a predetermined value for said at least one of said amount of change and said speed of change of the lighting region.

10. A head lamp device for a vehicle capable of changing a lighting region in front of the vehicle in rightward and leftward directions, said device comprises:

a head lamp;

lighting region changing means for changing a lighting region of the head lamp;

operation state detecting means for detecting an operation state of the vehicle;

strain degree judging means for judging a degree of strain of the driver by analyzing information detected by said operation state detecting means; and control means for controlling said lighting region changing means based on information judged by said strain degree judging means, and said control means adjusts at least one of amount of change and speed of change of the lighting region in accordance with the detected degree of strain of the driver.

11. A head lamp device for a vehicle as claimed in claim 10, wherein said operation state detecting means includes a vehicle speed sensor for detecting vehicle speed, and said strain degree judging means judges the degree of strain of the driver by analyzing the vehicle speed detected by said vehicle speed sensor.

12. A head lamp device for a vehicle as claimed in claim 10, wherein said operation state detecting means includes a steering angle sensor for detecting a steering angle, and said strain degree judging means judges the degree of strain of the driver by analyzing the steering angle detected by said steering angle sensor.

13. A head lamp device for a vehicle as claimed in claim 10, wherein said operation state detecting means includes a turning movement sensor for detecting turning movement of a body of the vehicle, and said strain degree judging means judges the degree of strain of the driver by analyzing the turning movement detected by said turning movement sensor.

14. A head lamp device for a vehicle capable of changing a lighting region in front of the vehicle in rightward and leftward directions, said device comprises:

a head lamp:

lighting region changing means for changing the lighting region of the lamp;

map information outputting means for outputting map information representing a map;

present position detecting means for detecting a present position of a proper vehicle on the map;

strain degree judging means for judging a degree of strain of the driver based on said map information outputted by said map information outputting means and said present position of the proper vehicle detected by said present position detecting means; and control means for controlling said lighting region changing means based on information judged by said strain degree judging means, and said control means adjusts at least one of amount of change and speed of change of the lighting region in accordance with degree of strain of the driver judged from a state of road in front of the proper vehicle.

15. A head lamp device for a vehicle as defined in claim 14, wherein said strain degree judging means determines the state of the road in front of the proper vehicle based on said map information output by said map information outputting means and the present position of the proper vehicle detected by said present position detecting means.

* * * * *

UNITED STATES PATENT AND TRADEMARK OFFICE
CERTIFICATE OF CORRECTION

PATENT NO. : 5,931,572
DATED : 03 August 1999
INVENTOR(S) : Shinichiro Gotoh

It is certified that error appears in the above-identified patent and that said Letters Patent is hereby corrected as shown below:

Column 1, line 6, change "direction" to --directions--;
  line 10, change "vehicles" to --vehicle's--;
  line 37, change "drivers" to --driver's--; change "movement" to --movements--;
  line 38, before "lighting" insert --the--;
  line 54, after "lamp" insert a semicolon;
  line 58, change "base" to --based--.
Column 2, line 21, change "driven" to --driver--;
  line 23, change "base on of" to --based on--.
Column 3, line 4, change "base" to --based--;
  line 8, change "base" to --based--.
Column 4, line 6, change "action" to --actions--;
  line 60, after "constant" insert a period.
Column 5, line 8, after "leftward" change the period to a comma.
Column 6, line 18, after "speed" insert --measured by sensor 19--;
  line 26, change "supposed" to --judged--;
  line 29, before the period insert --detected using sensor 20--;
  line 46, before "may" insert --it--;
  line 55, begin a new paragraph with "Although".

Signed and Sealed this

Twenty-first Day of March, 2000

Q. TODD DICKINSON

Attest:

Attesting Officer

Commissioner of Patents and Trademarks